United States Patent
Park et al.

(10) Patent No.: US 8,149,398 B2
(45) Date of Patent: Apr. 3, 2012

(54) METHOD OF MEASURING GADOLINIA CONTENT USING INDUCTIVELY COUPLED PLASMA-ATOMIC EMISSION SPECTROMETRY

(75) Inventors: Chan-Jun Park, Daejon (KR); Pil-Sang Kang, Daejon (KR); Chul-Joo Park, Daejon (KR); Bum-Sik Koh, Daejon (KR); Jun-No Lee, Daejon (KR); Hyoung-Joong Kim, Daejon (KR)

(73) Assignee: Korea Nuclear Fuel Co., Ltd., Daejeon (KR)

( * ) Notice: Subject to any disclaimer, the term of this patent is extended or adjusted under 35 U.S.C. 154(b) by 217 days.

(21) Appl. No.: 12/732,174

(22) Filed: Mar. 25, 2010

(65) Prior Publication Data

US 2011/0134424 A1    Jun. 9, 2011

(30) Foreign Application Priority Data

Dec. 8, 2009    (KR) .................. 10-2009-0121072

(51) Int. Cl.
*G01J 3/30* (2006.01)
(52) U.S. Cl. ...................................... 356/316; 356/318
(58) Field of Classification Search .................. 356/316, 356/317
See application file for complete search history.

(56) References Cited

OTHER PUBLICATIONS

Analytical Methodology in Nuclear Fuel Cycle, AGENDA, Working Group1, Manchester 2009.
Analytical Methodology in Nuclear Fuel Cycle, WG 12 Agenda, Working Group1, Jun. 2009, ISO.
Park, Chul Joo et al., Introduction of KNF Method for Determination of Gd2O3 Content in Gd Fuel Pellets, Mar. 23, 2010, Korea Nuclear Fuel.
Analytical Methodology in the Nuclear Fuel Cycle, ISO/TC 85/SC 5 WG1 Meeting, Document N, Jun. 2, 2009, Manchester, UK.

*Primary Examiner* — Layla Lauchman
(74) *Attorney, Agent, or Firm* — Hershkovitz & Associates, LLC; Abraham Hershkovitz

(57) ABSTRACT

A method of measuring a gadolinia content using inductively coupled plasma-atomic emission spectrometry is provided. The method can include grinding sintered gadolinium using a percussion mortar to obtain a ground sample; warming the ground sample and then dissolving it with an acid solution to obtain dissolved gadolinia; diluting the dissolved gadolinia with distilled water to obtain a diluted gadolinia solution; measuring mass of each of a uranium element and a gadolinium element in the diluted gadolinia solution by a unit of ppm using the inductively coupled plasma-atomic emission spectrometry; and calculating a molar fraction of gadolinium from the diluted gadolinia solution and then calculating the gadolinia content using the molar fraction of gadolinium.

5 Claims, 1 Drawing Sheet

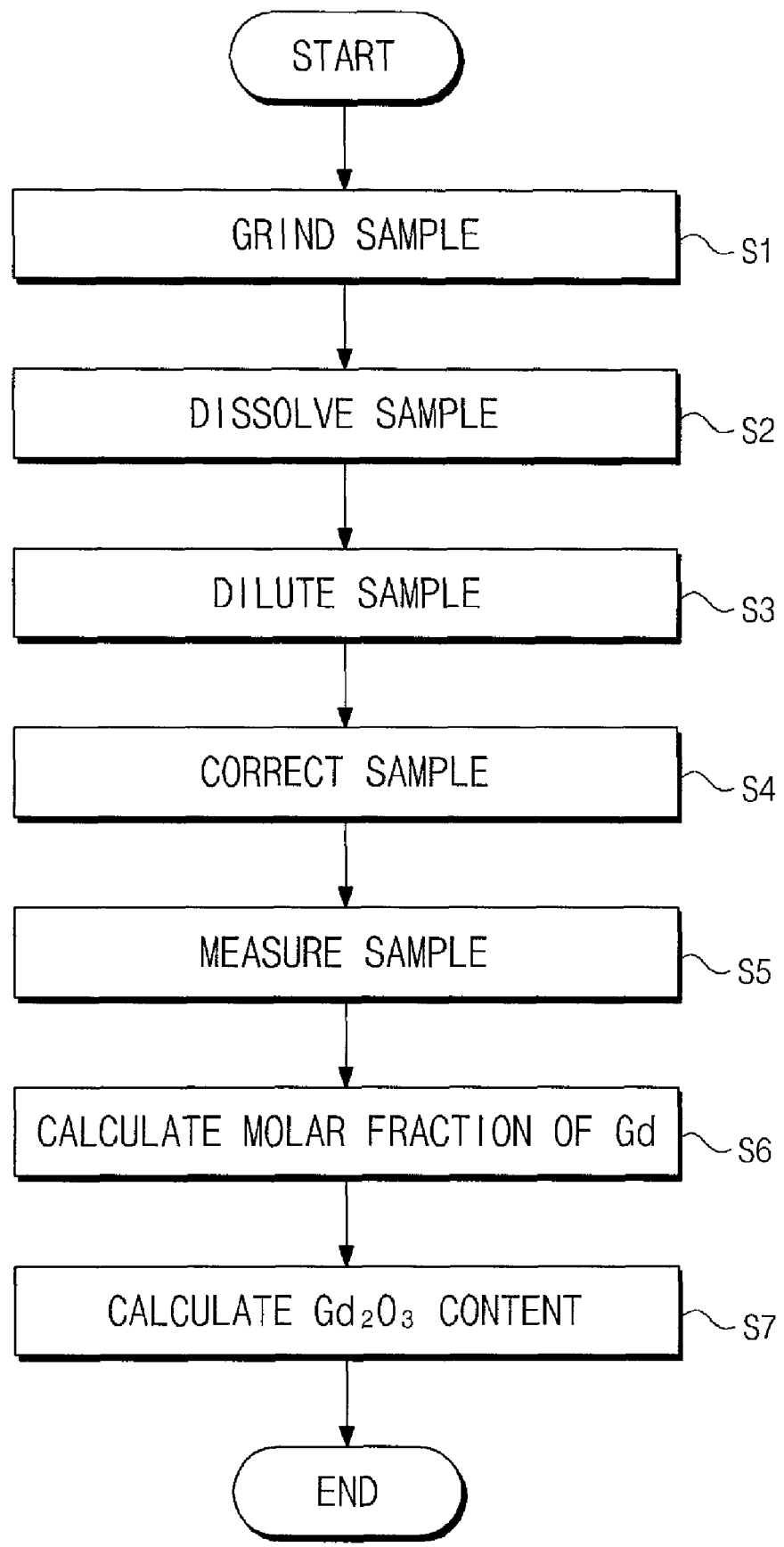

METHOD OF MEASURING GADOLINIA CONTENT USING INDUCTIVELY COUPLED PLASMA-ATOMIC EMISSION SPECTROMETRY

CROSS-REFERENCE TO RELATED APPLICATIONS

The present application claims priority benefits under 35 U.S.C. §1.119 to KR10-2009-0121072 filed Dec. 8, 2009.

BACKGROUND OF THE INVENTION

1. Technical Field

The present invention relates to a method of measuring a gadolinia (gadolinium(III) oxide, $Gd_2O_3$) content in sintered a $UO_2$—$Gd_2O_3$ pellet (Gd pellet) using inductively coupled plasma-atomic emission spectrometry (ICP-AES).

2. Description of the Related Art

Nuclear fuel used in nuclear power plants varies depending on the kind of atomic reactor. Currently, the nuclear fuel, which is widely useful all over the world in a light water reactor, is uranium (U)-235 concentrated to about 2~5%. Also, natural U is used in a heavy water reactor, and U concentrated to about 26% is used as nuclear fuel in a fast breeder reactor.

In the use of nuclear fuel, a powder material of nuclear fuel is compacted in the form of a small cylinder, sintered and formed into pellets, after which the plurality of pellets thus formed is placed in fuel rods to manufacture nuclear fuel rods.

The manufactured nuclear fuel rods are collected and bundled thereafter. Then, the nuclear fuel bundles are mounted in an atomic reactor to induce fission. In the course of fission, a mass defect of atoms is converted into a large amount of thermal energy, which is then used to produce electrical energy.

In a fission chain reaction of U, neutrons cause U-235 atoms to fission. As such, two or three neutrons are emitted again. Then, the emitted neutrons cause other U-235 atoms to fission. The fission chain reaction takes place in this way. When the neutrons are generated by fission, fast neutrons having very high energy are also produced. The fast neutrons are converted into thermal neutrons having middle energy and then into thermal neutrons having low energy. The thermal neutrons having low energy then undergo once more an absorption procedure for inducing fission.

Because neutrons have no charges, they do not lose energy due to an electromagnetic action such as electrolytic dissociation when passing through a material, resulting in a high transmission capability. For this reason, neutrons are essentially used in inducing fission without being disturbed by repulsive force with atomic nuclei.

The neutrons having middle energy are highly apt to be absorbed by resonance absorption without fission. The neutrons slowly lose their energy by collision with atomic nuclei. As such, energy which is lost per collision increases in inverse proportion and the mass of atomic nucleus which is a target decreases.

This process of energy loss is called moderation, and a material which effectively causes moderation is referred to as a moderator. Specifically, in order to appropriately convert neutrons having high energy into neutrons having low energy, the moderator is used to make the neutrons collide with atomic nuclei.

Such a moderator is mainly exemplified by sintered Gd pellet (for flammable absorption rods). Whereas sintered $UO_2$ pellet functions to generate neutrons in an atomic reactor, the sintered Gd pellet is fuel for absorbing neutrons so as to effectively control the output distribution of an atomic reactor. While the development of techniques for long-term operation of atomic power plants and highly combustible nuclear fuel continue to grow, the use of the sintered Gd pellet has recently been increasing. Such sintered Gd has been mostly dependent on importation to date, but is gaining success in localization. As such, localization requires the development of novel detection techniques and the establishment of test procedures.

Accordingly, methods of the measuring $Gd_2O_3$ content using X-ray fluorescence (XRF) have been conventionally used. Specifically, a $UO_2$—$Gd_2O_3$ sample is dissolved in a nitric acid and then added with samarium (Sm). The prepared $UO_2$—$Gd_2O_3$ sample is placed in a cell, and is then irradiated with X-rays as a radioactive light source and thus excited, so that elements of the sample absorb primary light rays and are thus excited, thereby emitting their characteristic type and X-rays. From Gd and Sm elements among the emitted elements, specific X-rays are counted, and spectral intensity is measured using a detector. The $Gd_2O_3$ content may be determined by a ratio of the Gd elements relative to Sm elements.

However, the above method is difficult to precisely detect the $Gd_2O_3$ content attributable to interference between U and Gd.

SUMMARY OF THE INVENTION

Therefore, the present invention has been made keeping in mind the above problems encountered in the related art, and the present invention is intended to provide a method of measuring a $Gd_2O_3$ content using ICP-AES so as to precisely determine the $Gd_2O_3$ content in a sintered $UO_2$—$Gd_2O_3$ pellet.

An aspect of the present invention provides a method of measuring a $Gd_2O_3$ content using ICP-AES, including grinding a sintered Gd pellet using a percussion mortar to obtain a ground sample; warming the ground sample and then dissolving it with a nitric acid solution to obtain dissolved $Gd_2O_3$; diluting the dissolved $Gd_2O_3$ with distilled water to obtain a diluted $Gd_2O_3$ solution; measuring mass (ppm) of each of U and Gd elements in the diluted $Gd_2O_3$ solution using the ICP-AES; and calculating a molar fraction of Gd from the diluted $Gd_2O_3$ solution and then calculating the $Gd_2O_3$ content using the molar fraction of Gd.

BRIEF DESCRIPTION OF THE DRAWING

FIG. 1 is a block flowchart showing a process of measuring a $Gd_2O_3$ content using ICP-AES according to the present invention.

DETAILED DESCRIPTION OF EMBODIMENTS

Hereinafter, a detailed description will be given of a method of measuring a $Gd_2O_3$ content using ICP-AES according to the present invention.

As shown in FIG. 1, the method of measuring the $Gd_2O_3$ content according to the present invention can include grinding (S1), dissolution (S2), dilution (S3), correction (S4), measurement (S5), and calculation (S6) (S7).

Specifically, in the grinding (S1), a sintered Gd pellet is grounded to an appropriate size using a percussion mortar, thus obtaining a ground sample.

In the dissolution (S2), the ground sample is dissolved in an appropriate amount of a nitric acid solution which is able to dissolve the sample.

In the dilution (S3), the $Gd_2O_3$ solution dissolved by the nitric acid solution is diluted to an appropriate concentration using distilled water. In order to measure the $Gd_2O_3$ content in $UO_2$—$Gd_2O_3$ nuclear fuel, the $Gd_2O_3$ solution is diluted with the distilled water up to an analytical concentration range of U and Gd elements. The analytical concentration range may be applied to about 10,000 times dilution in consideration of the ability of an ICP-AES instrument to detect elements.

In the correction (S4), the U and Gd contents of the diluted solution are respectively corrected by the ICP-AES.

In the measurement (S5), both the mass of U element and the mass of Gd element of the corrected sample are measured by a unit of ppm using the ICP-AES.

In the calculation (S6), the molar fraction of Gd from the diluted $Gd_2O_3$ solution is calculated. Specifically, the molar fraction of Gd in the sample solution is determined using the measured mass of U and Gd elements.

In the calculation (S7), the $Gd_2O_3$ content is calculated using the calculated molar fraction of Gd. The molar fraction of Gd is substituted into the following stoichiometric equation, to determine the $Gd_2O_3$ content.

The chemical reaction of the sintered Gd pellet is defined as follows.

$$2(1-y)UO_2 + yGd_2O_3 + \frac{y}{2}O_2 = 2(U_{1-y}, Gd_y)O_2$$

$$\text{number of moles of chemical species } A = \frac{\text{wt } A \text{ (g)}}{fw\ A \text{ (g/mol)}},$$

* $fw$ (formula weight):

$fw\ (Gd) = 157.25,\ fw\ (U) = 238.03,\ fw\ (O) = 15.9995$ $fw\ (UO_2) = 270.03,\ fw\ (Gd_2O_3) = 362.498$ $$y(\text{molar fraction of } Gd) = \frac{\frac{Gd}{157.25}}{\frac{Gd}{157.25} + \frac{U}{238.03}}$$

$$\begin{aligned}Gd_2O_3 \text{ content } (\%) &= \frac{\text{wt } (Gd_2O_3)}{\text{wt } (UO_2) + \text{wt } (Gd_2O_3)} \times 100 \\ &= \frac{y \times fw\ (Gd_2O_3)}{2 \times (1-y) \times fw\ (UO_2) + y \times fw\ (Gd_2O_3)} \times 100 \\ &= \frac{y \times 362.498}{2 \times (1-y) \times 270.03 + y \times 362.498} \times 100\end{aligned}$$

Specifically, a molar fraction, which shows a concentration of one component in a material system including two or more components, is represented by a ratio of the number of moles of any component to the total number of moles of all components. The value obtained by dividing the number of moles of any component by the total number of moles of all components is to be a molar fraction, and the molar fraction of each component may be determined. The calculated molar fraction of Gd is substituted into the above equation, thus easily determining the $Gd_2O_3$ content.

On the other hand, in order to measure the Gd element in the $UO_2$—$Gd_2O_3$ nuclear fuel using the ICP-AES, the U element and Gd element should be chemically separated because of spectroscopic interference therebetween. However, it is not easy to chemically separate such elements in the $UO_2$—$Gd_2O_3$ nuclear fuel. Even if being separated, a period of time required for such separation is lengthened and an accurate analysis is difficult. However, when the method based on the stoichiometric equation according to the present invention is applied, even when a sample is not accurately quantitatively weighed, the U element and Gd element are measured in the same sample using the ICP-AES, thus determining the molar fraction of Gd, which is then substituted into the stoichiometric equation, thereby determining the accurate $Gd_2O_3$ content.

EXAMPLE

1) One or more sintered Gd bodies (three in the present example) having different $Gd_2O_3$ contents were grounded using a percussion mortar, and then sampled to an appropriate amount.

2) Six random samplings of the ground Gd having different $Gd_2O_3$ contents were carried out, and about 0.10 g thereof was weighed using an analytical balance and then placed in a beaker. 10 ml of nitric acid was added thereto at 1:1, after which the beaker was covered and warmed so that the mixture therein was dissolved. Also, 10 ml of nitric acid was further added thereto at 1:1, as necessary, thus completely dissolving the sample.

3) The completely dissolved sample was transferred into a 1 l flask and then diluted with distilled water (about 10,000 times dilution in consideration of the ability of the ICP-AES instrument to detect U and Gd elements).

4) The U and Gd contents of the diluted solution were respectively corrected by the ICP-AES. With reference to Tables 1 to 3 below, because the measured U component did not exceed 100 ppm and the Gd component did not exceed 10 ppm, the U component was corrected by a 100 ppm U standard solution, and the Gd component was corrected by a 10 ppm Gd standard solution.

5) Both U element and Gd element of the corrected sample were measured.

6) The molar fraction of Gd in the sample solution was determined using the measured U and Gd elements.

7) The molar fraction of Gd was substituted into a stoichiometric equation, thus determining the $Gd_2O_3$ content.

After the U and Gd elements in the sintered Gd ($Gd_2O_3$ content: 4%, 6%, 8%) samples were analyzed using the ICP-AES in this way, a series of tests for analyzing the $Gd_2O_3$ content by the derived equation with the measured values were performed. The results are shown in Tables 1 to 3 below.

TABLE 1

| Sample No. | Gd(Yppm) | U(Xppm) | Molar Fraction of Gd | $Gd_2O_3$ Content (%) |
|---|---|---|---|---|
| 1 | 3.10 | 74.2 | 0.0595 | 4.07 |
| 2 | 3.10 | 74.3 | 0.0594 | 4.07 |
| 3 | 3.09 | 74.2 | 0.0593 | 4.06 |
| 4 | 3.09 | 74.2 | 0.0593 | 4.06 |
| 5 | 3.11 | 73.8 | 0.0600 | 4.11 |
| 6 | 3.11 | 73.3 | 0.0603 | 4.13 |
| Max. Value | 3.11 | 74.30 | 0.060 | 4.13 |
| Min. Value | 3.09 | 73.30 | 0.059 | 4.06 |
| Mean (x) | 3.10 | 74.00 | 0.060 | 4.082 |
| Standard Deviation (s) | 0.0089 | 0.3847 | 0.0004 | 0.0300 |
| Standard Error | | | | 0.0122 |
| Relative Standard Deviation | | | | 0.73% |
| Relative Mean Error | | | | 2.06% |
| Number of Samples (n) | | | | 6 |
| % $Gd_2O_3$ (90%) UCL | | | | 4.11 |
| LCL | | | | 4.06 |
| % $Gd_2O_3$ (90/90) UTL | | | | 4.18 |
| LTL | | | | 3.99 |

[$Gd_2O_3$ content specification = ±nominal value × 5%]

TABLE 2

| Sample No. | Gd(Yppm) | U(Xppm) | Molar Fraction of Gd | $Gd_2O_3$ Content (%) |
|---|---|---|---|---|
| 1 | 4.66 | 73.9 | 0.0871 | 6.02 |
| 2 | 4.65 | 73.7 | 0.0872 | 6.02 |
| 3 | 4.65 | 73.9 | 0.0870 | 6.01 |
| 4 | 4.65 | 73.9 | 0.0870 | 6.01 |
| 5 | 4.66 | 73.6 | 0.0875 | 6.04 |
| 6 | 4.67 | 73.6 | 0.0876 | 6.06 |
| Max. Value | 4.67 | 73.90 | 0.088 | 6.06 |
| Min. Value | 4.65 | 73.60 | 0.087 | 6.01 |
| Mean (x) | 4.66 | 73.77 | 0.087 | 6.027 |
| Standard Deviation (s) | 0.0082 | 0.1506 | 0.0003 | 0.0192 |
| Standard Error | | | | 0.0078 |
| Relative Standard Deviation | | | | 0.32% |
| Relative Mean Error | | | | 0.45% |
| Number of Samples (n) | | | | 6 |
| % $Gd_2O_3$ (90%) UCL | | | | 6.04 |
| LCL | | | | 6.01 |
| % $Gd_2O_3$ (90/90) UTL | | | | 6.09 |
| LTL | | | | 5.97 |

[$Gd_2O_3$ content specification = ±nominal value × 5%]

TABLE 3

| Sample No. | Gd(Yppm) | U(Xppm) | Molar Fraction of Gd | $Gd_2O_3$ Content (%) |
|---|---|---|---|---|
| 1 | 7.05 | 82.60 | 0.1144 | 7.98 |
| 2 | 7.05 | 82.60 | 0.1144 | 7.98 |
| 3 | 7.02 | 82.30 | 0.1144 | 7.97 |
| 4 | 7.03 | 82.70 | 0.1140 | 7.95 |
| 5 | 7.04 | 82.60 | 0.1143 | 7.97 |
| 6 | 7.02 | 82.70 | 0.1139 | 7.94 |
| Max. Value | 7.05 | 82.70 | 0.114 | 7.98 |
| Min. Value | 7.02 | 82.30 | 0.114 | 7.94 |
| Mean (x) | 7.04 | 82.58 | 0.114 | 7.965 |
| Standard Deviation (s) | 0.0138 | 0.1472 | 0.0002 | 0.0169 |
| Standard Error | | | | 0.0069 |
| Relative Standard Deviation | | | | 0.21% |
| Relative Mean Error | | | | 0.43% |
| Number of Samples (n) | | | | 6 |
| % $Gd_2O_3$ (90%) UCL | | | | 7.98 |
| LCL | | | | 7.95 |
| % $Gd_2O_3$ (90/90) UTL | | | | 8.02 |
| LTL | | | | 7.91 |

[$Gd_2O_3$ content specification = ±nominal value × 5%]

Table 1 shows a $UO_2+Gd_2O_3$ content (4.0%) specification, Table 2 shows a $UO_2+Gd_2O_3$ content (6.0%) specification and Table 3 shows a $UO_2+Gd_2O_3$ content (8.0%) specification.

In order to reduce an analysis error occurring in the analysis process, the analytical instrument was corrected by U and Gd standard solutions, and the sintered Gd bodies (three) having different $Gd_2O_3$ contents (4%, 6%, 8%) were grounded using a percussion mortar, six samplings to a very small amount (about 0.1 g) were carried out for each of the ground Gd having different $Gd_2O_3$ contents, and at least three measurements of each sample were repeated.

The method according to the present invention is advantageous because a very small amount (about 0.1 g) of sample is used, thus shortening a period of time required to prepare a sample and reducing errors due to a sample pre-treatment (pipetting, weighing), with exhibiting high analytical sensitivity.

Also, reproducibility in repeated analysis of the same sample is high. As a result of statistically analyzing the $Gd_2O_3$ content, an individual and lot specifications are satisfied. Thus, the method according to the present invention can be seen to be adapted to analyze the $Gd_2O_3$ content in the sintered Gd.

As described hereinbefore, the present invention provides a method of measuring the $Gd_2O_3$ content using the ICP-AES. According to the present invention, the $Gd_2O_3$ content in the sintered Gd pellet can be precisely measured by the ICP-AES. Also, because a very small amount (about 0.1 g) of sample can be used, a period of time required to prepare a sample can be shortened, and the error due to the sample pre-treatment (pipetting, weighing) can be reduced, with achieving high analytical sensitivity.

Although the embodiments of the present invention have been disclosed for illustrative purposes, those skilled in the art will appreciate that a variety of different modifications, additions and substitutions are possible, without departing from the scope and spirit of the invention as disclosed in the accompanying claims. Accordingly, such modifications, additions and substitutions should also be understood as falling within the scope of the present invention.

What is claimed is:

1. A method of measuring a gadolinia content using inductively coupled plasma-atomic emission spectrometry, the method comprising:
    grinding sintered gadolinium using a percussion mortar to obtain a ground sample;
    warming the ground sample and then dissolving it with an acid solution to obtain dissolved gadolinia;
    diluting the dissolved gadolinia with distilled water to obtain a diluted gadolinia solution;
    measuring mass of each of a uranium element and a gadolinium element in the diluted gadolinia solution by a unit of ppm using the inductively coupled plasma-atomic emission spectrometry; and
    calculating a molar fraction of gadolinium from the diluted gadolinia solution and then calculating the gadolinia content using the molar fraction of gadolinium.

2. The method as set forth in claim 1, wherein the dissolving is performed by dissolving the ground sample with a nitric acid solution at a 1:1 ratio.

3. The method as set forth in claim 1, further comprising correcting a uranium component by a 100 ppm uranium standard solution, after diluting the dissolved gadolinia.

4. The method as set forth in claim 1, further comprising correcting a gadolinium component by a 10 ppm gadolinium standard solution, after diluting the dissolved gadolinia.

5. A method of measuring a gadolinia content using inductively coupled plasma-atomic emission spectrometry, the method comprising:
    grinding sintered gadolinium using a percussion mortar to obtain a ground sample;
    warming the ground sample and then dissolving it with an acid solution to obtain dissolved gadolinia;
    diluting the dissolved gadolinia with distilled water to obtain a diluted gadolinia solution;
    measuring mass of each of a uranium element and a gadolinium element in the diluted gadolinia solution by a unit of ppm using the inductively coupled plasma-atomic emission spectrometry;
    calculating a molar fraction of gadolinium from the diluted gadolinia solution and then calculating the gadolinia content using the molar fraction of gadolinium;
    correcting a uranium component by a 100 ppm uranium standard solution, after diluting the dissolved gadolinia; and
    correcting a gadolinium component by a 10 ppm gadolinium standard solution, after diluting the dissolved gadolinia, wherein the dissolving is performed by dissolving the ground sample with a nitric acid solution at a 1:1 ratio.

* * * * *